United States Patent
Ranson et al.

(10) Patent No.: US 7,338,795 B2
(45) Date of Patent: *Mar. 4, 2008

(54) BIODESULFURIZATION OF HYDROCARBONS

(75) Inventors: Isora Ranson, San Antonio (VE); Carmen M. Rivas, San Antonio (VE)

(73) Assignee: Intevep, S.A. (VE)

( * ) Notice: Subject to any disclaimer, the term of this patent is extended or adjusted under 35 U.S.C. 154(b) by 579 days.

This patent is subject to a terminal disclaimer.

(21) Appl. No.: 10/372,519

(22) Filed: Feb. 24, 2003

(65) Prior Publication Data

US 2003/0170874 A1    Sep. 11, 2003

Related U.S. Application Data

(63) Continuation-in-part of application No. 10/096,405, filed on Mar. 11, 2002, now Pat. No. 6,808,919.

(51) Int. Cl.
*C12S 1/02* (2006.01)
(52) U.S. Cl. .................... 435/282; 435/252.1; 435/829
(58) Field of Classification Search ................ 435/282, 435/252.1, 829
See application file for complete search history.

(56) References Cited

U.S. PATENT DOCUMENTS

| 2,521,761 | A | * | 9/1950 | Strawinski | 435/282 |
| 2,574,070 | A | * | 11/1951 | Strawinski | 435/282 |
| 5,358,870 | A | * | 10/1994 | Monticello et al. | 435/282 |
| 6,808,919 | B2 | * | 10/2004 | Ranson et al. | 435/282 |

FOREIGN PATENT DOCUMENTS

EP    558682 B1 *    6/1998

* cited by examiner

*Primary Examiner*—William H. Beisner
(74) *Attorney, Agent, or Firm*—Bachman & LaPointe, P.C.

(57) ABSTRACT

A process for treating liquid hydrocarbon, includes the steps of providing a liquid hydrocarbon containing complex sulfur-containing compounds, providing a bioactive material selected from or derived from members of genus *Alcaligenes*; and exposing the liquid hydrocarbon to the bioactive material under effective conditions such that the bioactive material interacts with the complex sulfur compounds and transforms the organic sulfur-containing compounds into inorganic sulfur compounds.

18 Claims, 6 Drawing Sheets

BIODESULFURIZATION OF HYDROCARBONS

CROSS-REFERENCE TO RELATED APPLICATION

This application is a Continuation-In-Part of U.S. patent application Ser. No. 10/096,405 filed Mar. 11, 2002, now U.S. Pat. No. 6,808,919.

BACKGROUND OF THE INVENTION

The invention relates to biodesulfurization of hydrocarbons and, more particularly, to a bioactive material and method using same for breaking down complex organic sulfur-containing compounds within a hydrocarbon so as to facilitate removal of same.

Sulfur content in hydrocarbons is an important concern for numerous reasons, particularly when the hydrocarbon is to be used as a fuel. Numerous methods, systems and compositions are known and used for removal of sulfur from the hydrocarbon. Although these are somewhat effective, problems remain.

Sulfur is particularly difficult to effectively remove when it is present in organic sulfur-containing compounds, such as dibenzothiophene. The normal degradative pathway for dibenzothiophene (DBT) results in a different, but still complex organic sulfur-containing compound, such as 3-hydroxy-2-formilbenzothiophene, and removal of this compound undesirably removes carbon from the hydrocarbon.

In light of the foregoing, it is clear that the need remains for addressing the removal of sulfur when present in complex organic compounds.

It is therefore the primary object of the present invention to provide a method and bioactive material which are well suited to this removal.

It is a further object of the present invention to provide a method and bioactive material which are useful for reducing the C15+ fraction of a hydrocarbon, and thereby further improving the characteristics of same.

Other objects and advantages of the present invention will appear hereinbelow.

SUMMARY OF THE INVENTION

In accordance with the present invention, a process is provided for treating liquid hydrocarbon, which process comprises the steps of providing a liquid hydrocarbon containing organic sulfur-containing compounds; providing a bioactive material selected from or derived from members of genus *Alcaligenes*; and exposing said liquid hydrocarbon to said bioactive material under effective conditions such that said bioactive material interacts with said organic sulfur-containing compounds and transforms said organic sulfur-containing compounds into inorganic sulfur compounds. These inorganic sulfur compounds can then be more easily separated from the hydrocarbon.

A bioactive material is also provided.

In further accordance with the present invention, a modified strain or genetic bacteria platform is provided which is derived from *Alcaligenes*, is viable in oil, and is active in breaking down carbon-sulfur-carbon bonds in organic sulfur-containing compounds.

BRIEF DESCRIPTION OF THE DRAWINGS

A detailed description of preferred embodiments of the present invention follows, with reference to the attached drawings, wherein.

DETAILED DESCRIPTION

The invention relates to a bioactive material and a method or process for using same in treating hydrocarbons to transform complex organic sulfur compounds into more easily removable inorganic sulfur compounds, thereby making sulfur removal easier.

In accordance with the present invention, it has been found that members of the genus *Alcaligenes*, under certain conditions, have excellent activity toward attacking carbon-sulfur-carbon bonds in complex organic sulfur-containing compounds, thereby leading to inorganic sulfur compounds as desired. The species *Alcaligenes xylosoxidans* has been found to be particularly effective at this selective transformation. Further, *Alcaligenes xylosoxidans* can be conditioned or modified into a derivative which is viable in oil and has excellent desired sulfur activity for example in conversion of DBT to inorganic sulfur compounds. Cells of this material have been deposited under the Budapest Treaty on Sep. 16, 2002. ATCC whose address is 1081 University Boulevard, Manassas, Va. 20110-2209 and has received Patent Deposit Designation PTA-4669. A copy of the Deposit Receipt from ATCC has been forwarded to the U.S. Patent and Trademark Office in parent application Ser. No. 10/096,405, now U.S. Pat. No. 6,808,919.

The bioactive material of the present invention preferably includes cells from *Alcaligenes xylosoxidans* strains and more specifically a derivative, or an enzymatic extract, from the active cells which is biocatalytically active on organic sulfur compounds as described above. This extract contains an oxidase enzyme believed to be particularly active.

In accordance with the present invention, the bioactive material as described above is advantageously used to transform organic sulfur-containing compounds contained in hydrocarbons into inorganic sulfur compounds, which are more readily removed from the hydrocarbon. Further, these inorganic compounds have an affinity toward water and, when the treatment process is carried out with an emulsion, the inorganic sulfur compounds are formed in or travel to the water phase further facilitating separation. Still further, this separation of sulfur is accomplished without removal of desirable constituents from the hydrocarbon.

Typical hydrocarbons which can advantageously be treated in accordance with the present invention include any liquid hydrocarbon or hydrocarbon slurry which contains organic sulfur compounds. Preferred hydrocarbons for such treatment include, among others, bitumen, heavy crude, medium crude, Diesel fuel, gasoline, coal slurry and mixtures thereof. Bitumen is particularly advantageously treated in accordance with the present invention since this hydrocarbon contains significant amounts of organic sulfur-containing compounds.

In accordance with the present invention, it has further been found that some strains of the bioactive material in accordance with the present invention are hydrophilic and lipophobic. As the mechanism is carried out by contacting the materials, this makes contacting of the bioactive material with hydrocarbon difficult. In accordance with the present invention, this problem is solved, when present, by forming a hydrocarbon in water emulsion of the hydrocarbon, and adding the bioactive material to the water, either before or after emulsion formation, such that the bioactive material is nevertheless in intimate contact with a major portion of the hydrocarbon.

Figure 1:
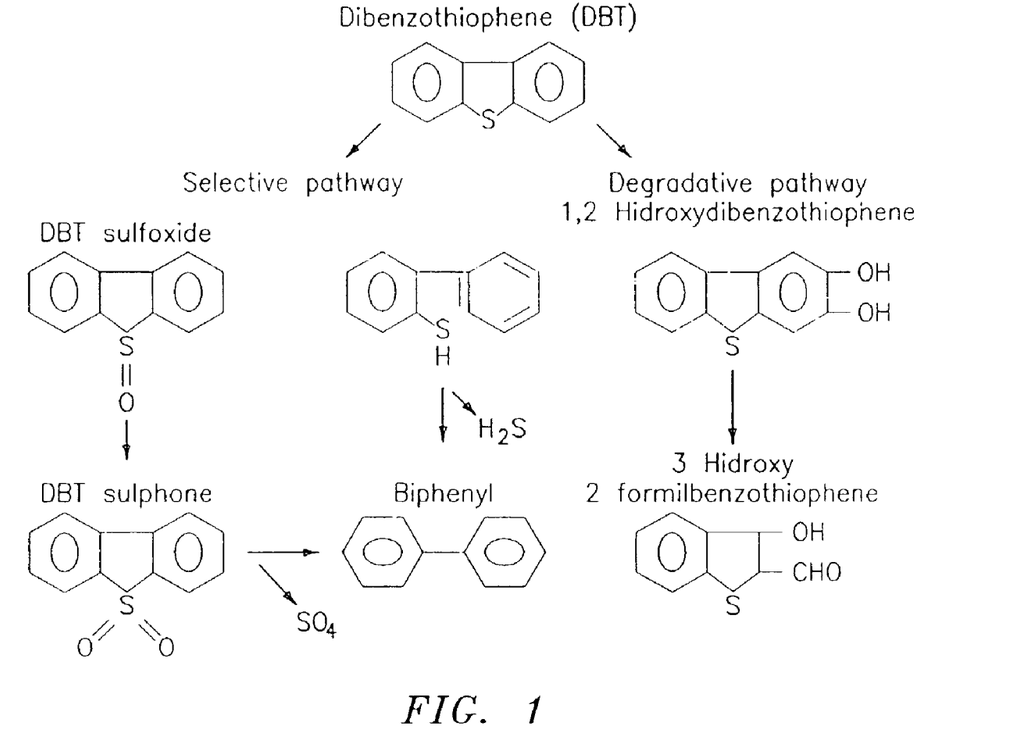
FIG. 1 schematically illustrates a selective pathway of DBT breakdown when treated in accordance with the invention, as well as a conventional degradative pathway.

As set forth above, the bioactive material in accordance with the present invention is particularly effective in attacking carbon-sulfur-carbon bonds of complex organic sulfur-containing compounds. For example, and as shown in FIG. 1, dibenzothiophene (DBT), when exposed to the bioactive material in accordance with the present invention, reacts along a selective pathway wherein the end result is a final product including biphenyl and inorganic sulfur compounds such as sulphates, hydrogen sulfide and the like. These inorganic sulfur-containing compounds are more readily separated from the hydrocarbon using conventional methods and equipment. Thus, in accordance with the present invention, the bioactive material provides activity along selective pathways which advantageously render sulfur in the hydrocarbon more easily removable.

FIG. 1 also illustrates, in the right hand portion of the figure, the degradative pathway experienced without a selective catalyst such as the bioactive material of the present invention. As shown, DBT may break down but this does not result in sulfur being moved to inorganic, less complex, and more easily removable compounds.

The bioactive material in accordance with the present invention is also active in breaking down other organic sulfur-containing compounds, such as alkylthiophenes, naphthobenzothiophene, dimethylthiopene, thionaphthene and the like. The mechanism of the bioactive material in accordance with the present invention advantageously allows for selective breaking down of such compounds, and any other compounds involving carbon-sulfur-carbon bonds, so as to transform the sulfur into inorganic sulfur compound form as desired.

The bioactive material and hydrocarbon in accordance with the present invention are advantageously exposed to each other, preferably at a concentration of at least about 1 mg/ml of total protein in the extract per ml of hydrocarbon of total emulsion, more preferably between about 1 mg/ml and about 5 mg/ml of total protein in the extract or ml of hydrocarbon of total emulsion, and at effective conditions, preferably a temperature between about 30° C. and about 50° C. and a pH of between about 7.0 and about 8.0, such that the complex sulfur-containing organic compounds are transformed as desired.

Conversion rates of dibenzothiophene, in accordance with the present invention, are advantageously at least about 70% wt., which results in a substantially facilitated sulfur removal from the hydrocarbon as desired. This advantageously transforms a substantial amount of DBT and other difficult-to-remove sulfur into more easily removed form, and further into a form which does not include carbon that is preferably left in the hydrocarbon.

The bioactive material was isolated from a soil and hydrocarbon sample which is typical of a local environment in Venezuela. A sample of this soil was then mixed with a mineral medium and dibenzothiophene so as to obtain a biomass from which the bacteria can be isolated. Utilizing known isolation techniques, this leads to identification of the genus and species. From this, a pure culture can be obtained and subjected to biochemical tests that confirm *Alcaligenes*, and further can be subjected to DNA testing which confirm *xylosoxidans* as the species.

From a pure culture of the material, biomass is further produced and subjected to centrifuge so as to separate cells which can be processed, for example using mechanical or other extraction methods, to obtain an enzymatic extract containing oxidase and possessing the activity discovered in accordance with the present invention. Using known methods, an inoculum is obtained from which a biomass is produced, and the desired extract is obtained from the biomass as more fully described below.

A process for extracting the particularly desirable enzymatic extract in accordance with the present invention can be conducted by first sterilizing a culture medium in a suitable vessel, for example at a pressure of 15 psi for 15 minutes at a temperature of 121° C.

The vessel is then preferably held at a fermentation temperature, preferably of about 30° C., and ventilated or exposed to a flow of air for about 1 hour, with air flow rate at the rate of about 1 liters per minute.

The vessel is preferably inoculated with the strain, for example in an amount of about 0.2% weight of the culture medium. The bacteria is then preferably allowed to incubate, for example at a temperature of 30° C., with agitation at 150 rpm, for a period of about 72 hours, and in a mineral medium containing organic sulfur, for example DBT, as the sole source of sulfur, and further with a glucose as a growth factor, for example in an amount of about 0.2% wt.

The material is then subjected to an incubation period for approximately 18-24 hours, without agitation, and with a flow of air preferably of about 2 liters per minute, and a temperature of about 30° C.

The incubated material is then advantageously subjected to centrifugation, for example at 10,000×g, for about 20 minutes, so as to recover the biomass material and separate material from which the extract is to be obtained.

This separated material is then re-suspended in a buffer solution of potassium phosphate (100 mM), having a pH of 7, and this suspension is subjected to a Braun homogenizer so as to rupture the cells.

The solution is then again subjected to centrifuge at 10,000×g, for an additional period of about 20 minutes, and supernatant material containing the desired enzymatic extract can then be withdrawn from the solution.

In further accordance with the invention, a genetic bacteria platform or derivative can be obtained from *Alcaligenes xylosoxidans* strain which is viable in oil, and which exhibits excellent levels of the desired sulfur activity. This can be accomplished by incubating the starting *Alcaligenes xylosoxidans* strain in a vessel with a suitable medium such as medium having the following composition (g/l) :$NaH_2PO_4$, 4; $K_2HPO_4$, 4; $NH_4Cl$, 2; $MgCl_2 \times 6\ H_2O$, 0.2; $CaCl_2 \times 2H_2O$, 0.001; $FeCl_3 \times 6H_2O$, 0.001; with 0.2% glucose as a growth factor, and further with limited sources of sulfur, most preferably the only source being in the form of dibenzothiophene (DBT). Following conditioning under these conditions, the conditioned *Alcaligenes xylosoxidans* strain can then be grown by further incubating preferably with exposure to a broth medium such as a meat extract/bacto-peptone medium. From the resulting product, different biomolecules can be obtained. Biomolecules so obtained can then be further incubated with exposure to additional microbial culture, and biomass material can be recovered by centrifuge.

Cells obtained in this manner can then be subjected to a lysis process, followed by elimination of nucleic acid through addition, for example, of manganese chloride. The supernatant, free of envelope debris, are recovered after centrifugation. The supernatant may contain active biomolecules, and protein content may therefore preferably be determined, for example by Folin fenol of Lowry methods. According to the invention, DBT conversion increases as protein concentration increases, with excellent results being obtained at protein concentrations of at least 1 mg/ml (protein/reaction mixture), preferably at least 3 mg/ml and most preferably at least 4 mg/ml.

These active biomolecules, derived from *Alcaligenes xylosoxidans*, show much greater activity at conversion of dibenzothiophene than the starting *Alcaligenes xylosoxidans* material. Thus, the extracted biomolecules or modified strain exhibits excellent activity toward breaking down the desired complex organic sulfur bonds so as to transform complex organic sulfur compounds into inorganic sulfur compounds as desired.

The following examples further demonstrate the bioactive material and use of same in accordance with the present invention.

EXAMPLE 1

In this example, an enzymatic extract of *Alcaligenes xylosoxidans* identified as INTS-1 was prepared in mixture with a hydrocarbon, with the pH varied between 7, 8 and 9, and the activity of the bioactive material was measured.

Figure 2:
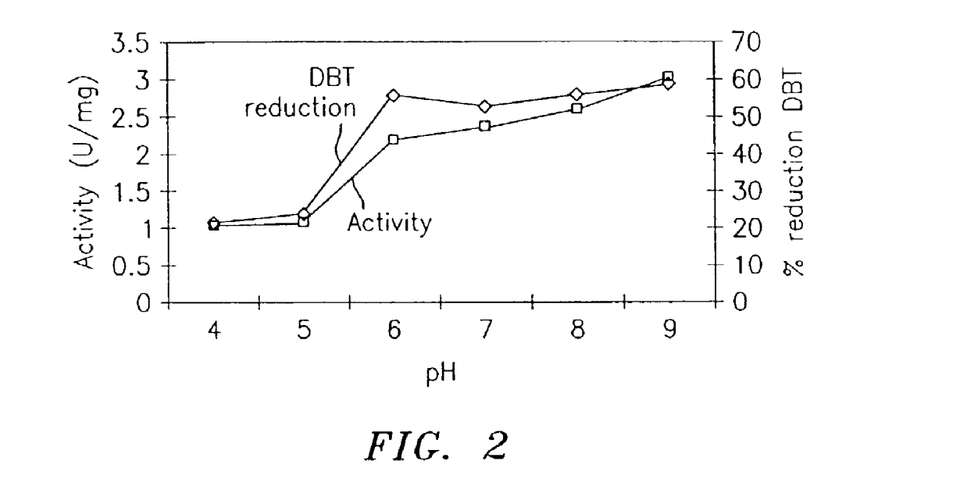
FIG. 2 illustrates activity and percent reduction in DBT as a function of pH in accordance with the present invention.

FIG. 2 shows activity for INTS-1 at various pH, along with per cent reduction in DBT.

As shown, best results are obtained at pH greater than 6 and up to 9.

Figure 3:
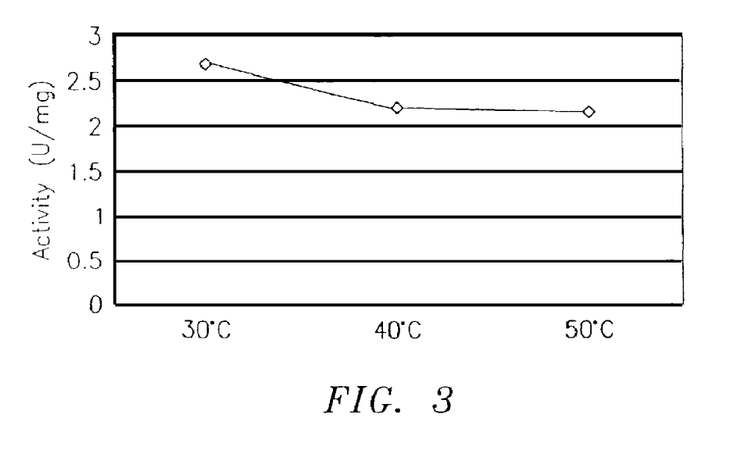
FIG. 3 illustrates activity over a range of temperatures in accordance with the present invention.

The bioactive material was then further evaluated, at pH of 7, and at temperatures between 30° C. and 50° C. FIG. 3 shows the results of this testing, and it can be seen that the material was effective between temperatures of 30° C. and 50° C.

Figure 4:
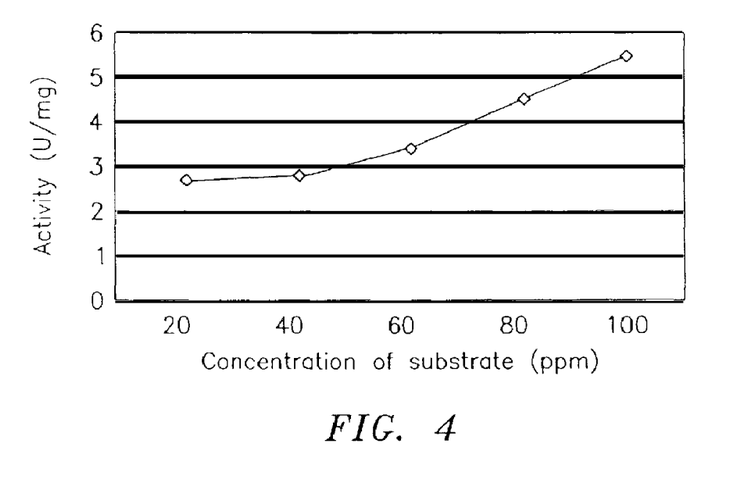
FIG. 4 illustrates activity as a function of concentration of a substrate in accordance with the present invention.

Activity of the strain as identified above was then measured for a fixed concentration of the enzymatic extract relative to increasing amounts of DBT substrate. FIG. 4 shows the results obtained, and the continuous increase in activity shows that saturation by the DBT substrate occurs at a value greater than 100 ppm.

Figure 5:
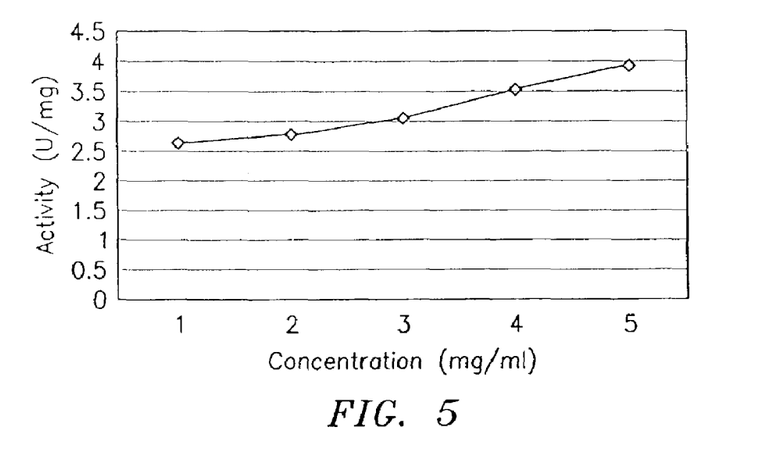
FIG. 5 illustrates activity as a function of concentration of the bioactive material.

Activity of the bioactive material as described above was then evaluated at different concentrations of an enzymatic extract per volume of hydrocarbon. FIG. 5 shows the results of this evaluation, and shows that activity of the material increases gradually above a concentration of 2 mg/ml. An optimum concentration of this strain is about 2 mg/ml depending upon whether the additional activity obtained at higher concentration is cost justified.

EXAMPLE 2

In this example, a hydrocarbon sample was obtained which contained dibenzothiophene (DBT), and was exposed to bioactive material in accordance with the present invention.

Figure 6:
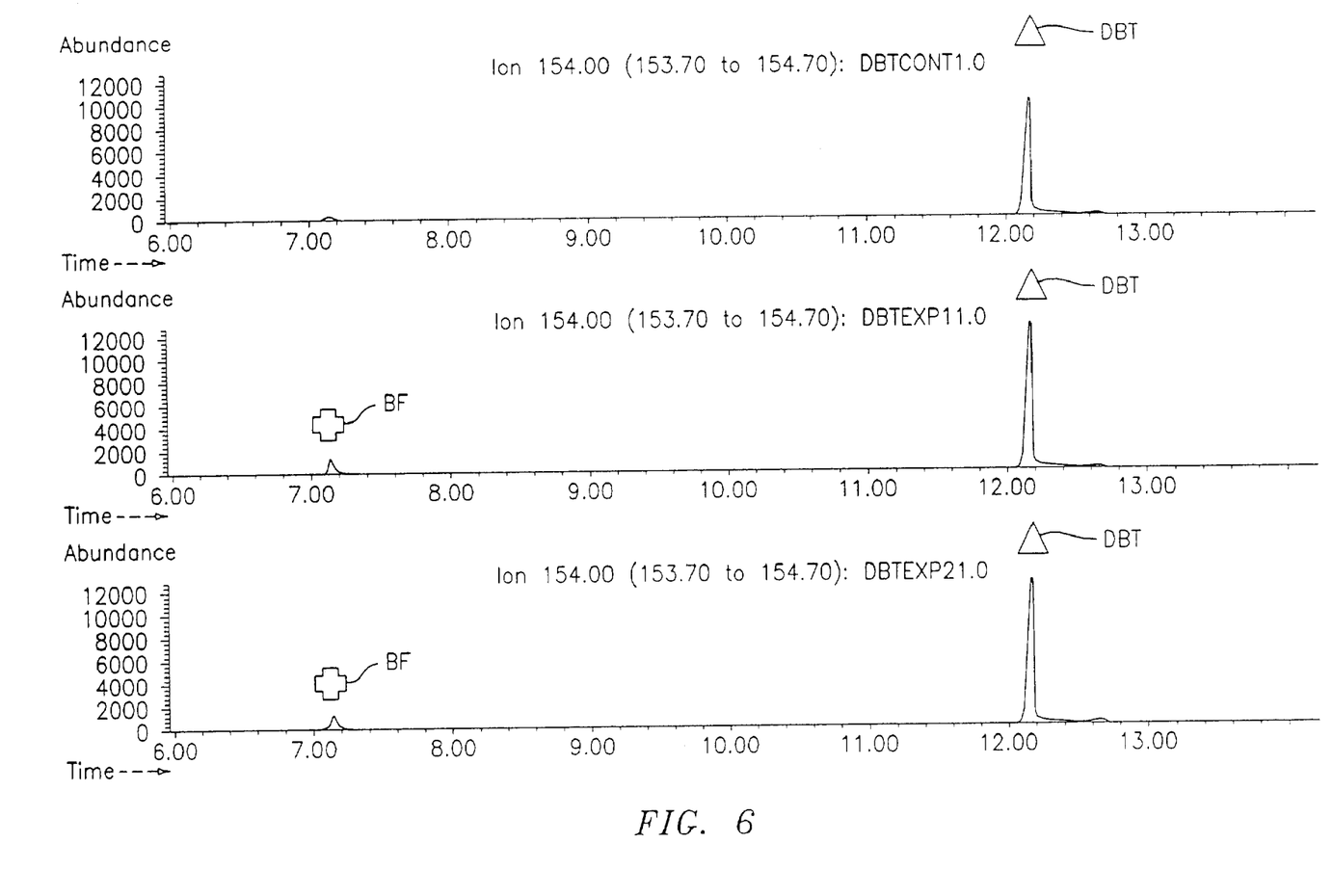
FIG. 6 illustrates data for a hydrocarbon before and after treatment to show the presence in the product of biphenyl.

FIG. 6 sets forth gas chromatography—mass spectrometry data for the starting product and finishing materials for two runs, namely "Experimental 1" and "Experimental 2", and a "Control" which contained no bioactive material. As set forth above, the catalytic activity of the bioactive material in accordance with the present invention breaks down DBT to form biphenyl (BF) as well as the desired inorganic sulfur compounds which are more readily removed. The second and third patterns shown in FIG. 6 clearly show a new spike appearing which corresponds to the identification of biphenyl (BF), thereby confirming that transformation of dibenzothiopene to biphenyl is occurring, as desired, and this confirms transformation of sulfur from the organic compound to inorganic compounds, also as desired.

Table 1 sets forth these results in table form as well.

TABLE 1

| | Area Relative (%) | |
|---|---|---|
| | DBT | BF |
| Control | 99.05 | 0.95 |
| Experimental 1 | 92.69 | 7.31 |
| Experimental 2 | 92.62 | 7.38 |

EXAMPLE 3

Figure 7:
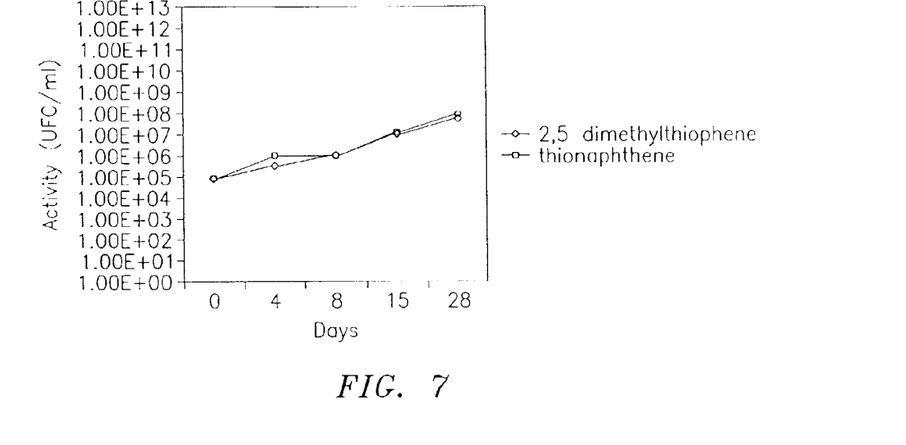
FIG. 7 shows bioactivity of the bioactive material of the present invention in connection with other organic sulfur compounds.

In this example, the same bioactive material as evaluated in Examples 1 and 2 was further evaluated in connection with activity on other organic sulfur compounds, namely dimethylthiopene and thionaphthene. FIG. 7 shows the relationship between incubation time in days and activity in connection with these two other organic sulfur compounds. As shown, the bioactive material in accordance with the present invention has activity toward breaking down these organic sulfur compounds as well.

EXAMPLE 4

In this example, a bitumen in water emulsion was prepared having a ratio of hydrocarbon to water of 70:30, and the hydrocarbon contained DBT, alkyl thiopenes and naphthabenzothiophene, as well as a substantial fraction of C16+ hydrocarbons.

Figure 8:
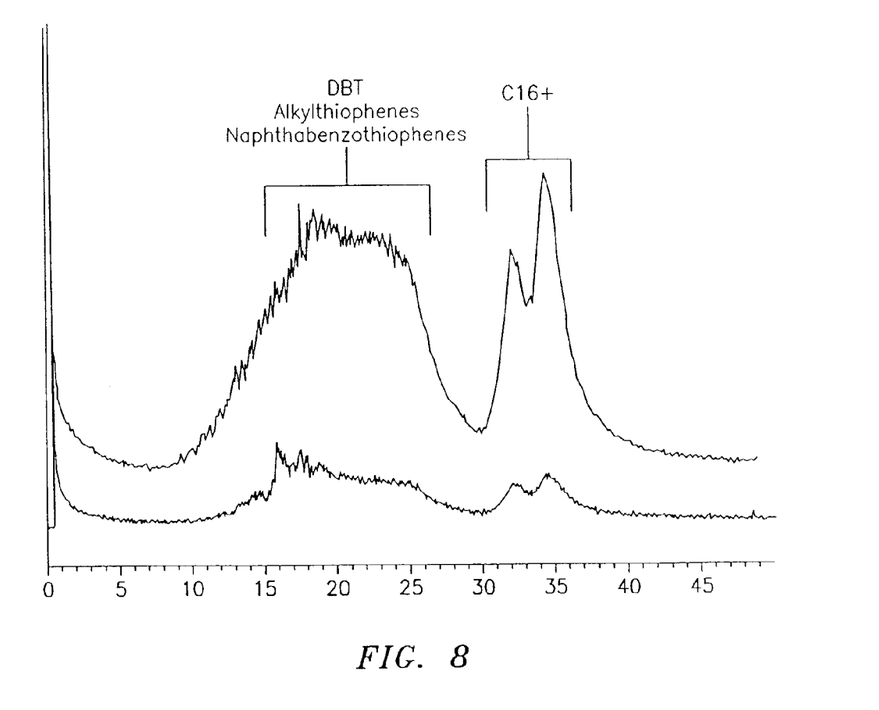
FIG. 8 shows excellent results obtained in treating a hydrocarbon in terms of reduction in organic sulfur compounds, as well as reduction in the C16+ fraction.

This hydrocarbon was treated using the bioactive material of the present invention, and an analysis of the starting hydrocarbon and final product are shown in FIG. 8. As shown, the organic sulfur compounds are substantially reduced, as is the C16+ fraction, all as desired in accordance with the present invention.

EXAMPLE 5

As set forth above, the hydrocarbon to water ratio of emulsions formed in accordance with the present invention can also effect the amount of sulfur removal.

Figure 9:
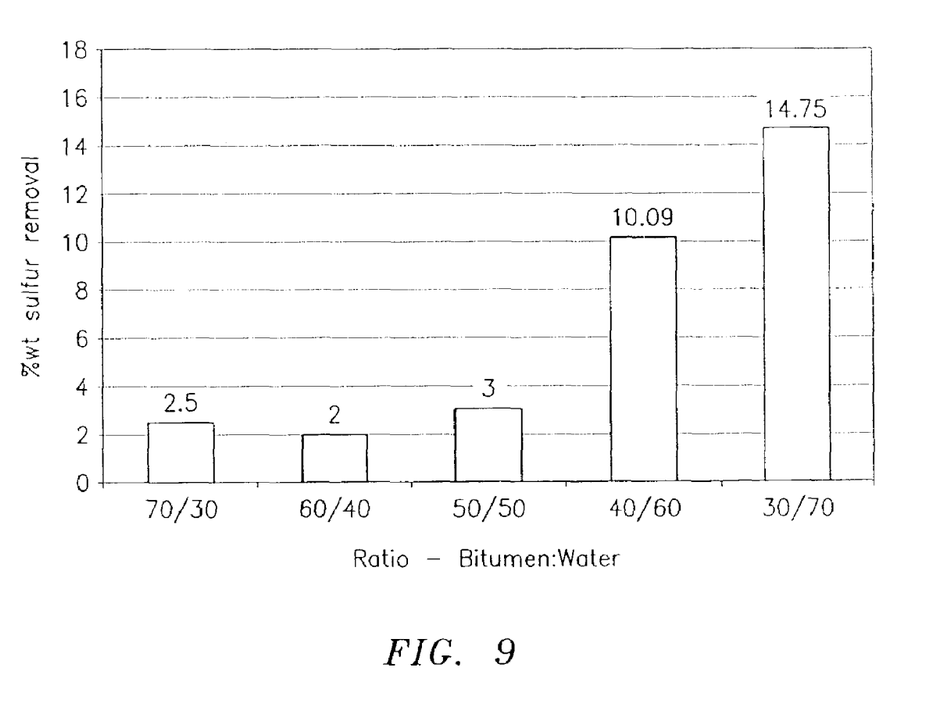
FIG. 9 shows sulfur removal results in connection with emulsions having different ratios of hydrocarbon to water.

Sulfur removal was evaluated for five different emulsions having ratios of hydrocarbon to water of between 70:30 and 30:70, and the results of this evaluation are set forth in FIG. 9.

As shown, the percentage removal of sulfur increases as the water content of the emulsion increases.

EXAMPLE 6

This example illustrates the conditioning of *Alcaligenes xylosoxidans* strain into the modified strain of the present invention.

First, a conditioning step was carried out as follows. *Alcaligenes xylosoxidans* strain was incubated for 72 hours at 30° C., in a 250 ml vessel, with 100 ml of medium having the following composition (g/l) :$NaH_2PO_4$, 4; $K_2HPO_4$, 4; $NH_4Cl$, 2; $MgCl_2 \times 6\ H_2O$, 0.2; $CaCl_2 \times 2H_2O$, 0.001; $FeCl_3 \times 6H_2O$, 0.001; with 0.2% glucose as a growth factor and 100 ppm dibenzothiophene (DBT) as the only source of sulfur.

Conditioned *Alcaligenes xylosoxidans* was then grown by incubating the strain for 24 hours at 30° C. and 150 rpm, in a 250 ml vessel, with 100 ml of broth medium consisting of (g/l): meat extract, 3, bacto-peptone, 5.

Biomolecules were produced by obtaining two different biomolecules from the growth product. 100 ml of each microbial culture were inoculated in 21 vessels containing 1 l of broth medium as identified above, and were incubated at 30° C. for 24 hours at 150 rpm. Biomass was recovered by centrifugation at 10,000 rpm, for 15 minutes, and the biomass was washed twice using 100 mM pH 7 phosphate buffer. The cells thus obtained were subjected to a lysis process, in which stirring was conducted using "Glasperlen" Nr. 31/14 0.10-0.11 mm pearls, with stirring being conducted in a Brown Homogenizer for 8 minutes at room temperature. Nucleic acids were eliminated by adding 0.05 ml of 1M $MnCl_2$. The supertanants, free of cell envelope debris, were recovered after centrifugation. These supernatants may contain active biomolecules, and their protein content was determined by the Folin fenol Lowry method. The biomolecules, or extract, were subjected to catalytic activity determination as described below.

Figure 10:
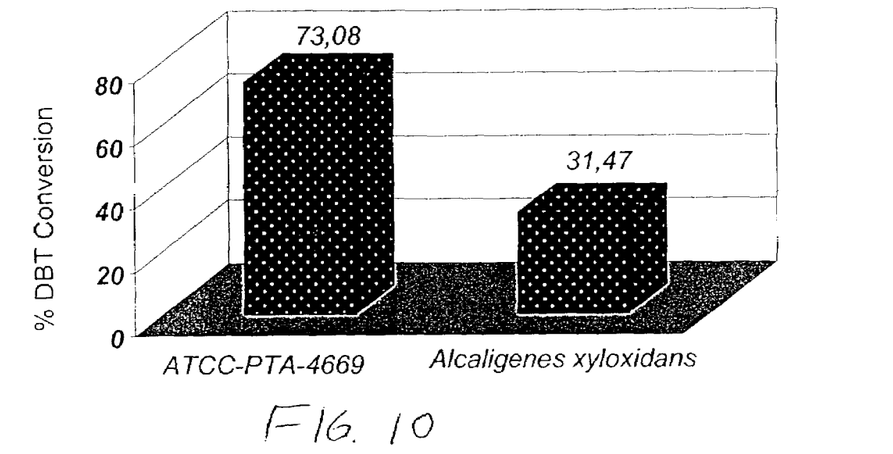
FIG. 10 illustrates DBT conversion for a starting *Alcaligenes xylosoxidans* strain and a strain modified according to the invention.

Tests were carried out on reaction mixtures containing 1 mg/ml of proteins, 100 ppm DBT in ethanol, and 1 mM NADH. The mixtures were incubated for 60 minutes at 30° C. and 100 rpm. The reaction was stopped by adding 200 ml of 1N HCl. Organic phase was extracted with dichloromethane 1:1, and the DBT concentration was determined by Gas Chromatography. Results, expressed as percent DBT converted, are shown in FIG. 10. As shown, the modified strain converted 73.08% of DBT, while the starting *Alcaligenes xylosoxidans* strain converted only 31.47%. Thus, the modified strain in accordance with the present invention definitely shows enhanced performance as compared to the basic strain.

EXAMPLE 7

Figure 11:
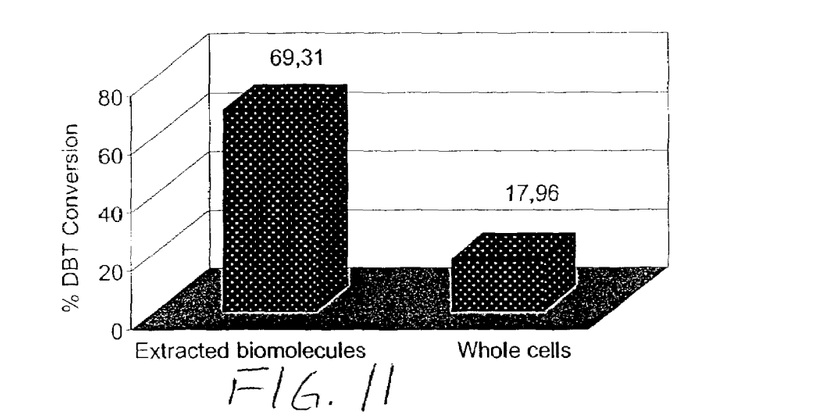
FIG. 11 illustrates DBT conversion for whole cells of the modified strain and also for extracted biomolecules of the modified strain.

Biodesulfurization catalytic activity was further determined as described, using whole cells of the modified strain, as well as the free-cell envelope extract material. Results of this testing are shown in FIG. 11, where it is illustrated that the extracted biomolecules in accordance with the present possess excellent DBT conversion rates.

EXAMPLE 8

In this example, the effect of protein content in the reaction mixture upon DBT conversion rates is illustrated.

Figure 12:
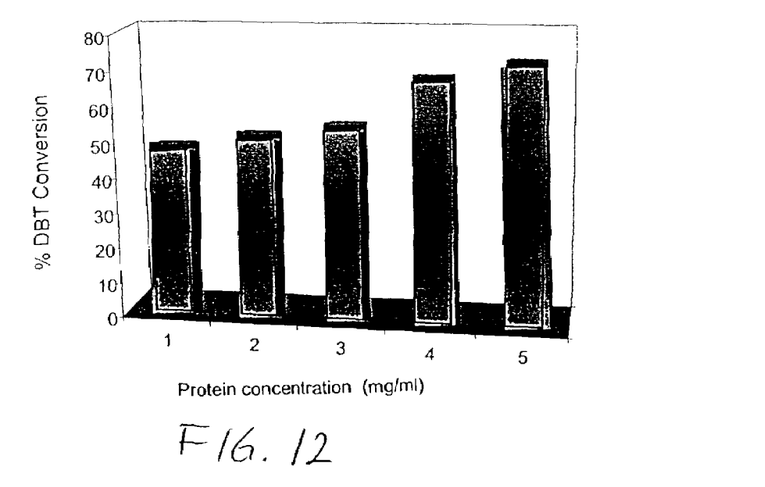
FIG. 12 illustrates DBT conversion rates obtained using different protein concentrations of extracted biomolecules according to the invention.

Extracted biomolecules were obtained as set forth above, and the protein content of same was determined. A suitable amount of the strain was then used in order to produce a protein content in the reaction mixture of between 1 and 5 mg/ml. FIG. 12 shows results obtained with each different level of protein concentration. As shown, as the protein concentration increases, DBT conversion also increases.

In accordance with the foregoing, it is clear that a bioactive material, and method for using same, have been provided which advantageously convert dibenzothiophene and other organic sulfur-containing compounds into inorganic sulfur compounds such as $SO_4$ compounds and $H_2S$, along with biphenyl hydrocarbons. This is advantageous in that the sulfur is then more easily removable when in inorganic form, as desired in accordance with the present invention.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed:

1. A process for treating a liquid hydrocarbon, comprising the steps of:
   providing a liquid hydrocarbon containing organic sulfur-containing compounds;
   providing a bioactive material comprising a derivative of *Alcaligenes xylosoxidans* INTS-1 (PTA 4669); and
   exposing said liquid hydrocarbon to said bioactive material under effective conditions such that said bioactive material interacts with said organic sulfur-containing compounds and transforms said organic sulfur-containing compounds into inorganic sulfur compounds, wherein the derivative is obtained by a process comprising incubating a strain of said *Alcaligenes xylosoxidans* with exposure to a broth medium.

2. The process of claim 1, wherein said bioactive material transforms said organic sulfur-containing compounds by breaking carbon-sulfur-carbon bonds therein.

3. The process of claim 1, further comprising the step of forming a hydrocarbon in water emulsion of said liquid hydrocarbon and wherein said exposing step comprises exposing said emulsion to said bioactive material.

4. The process of claim 3, wherein said step of forming said hydrocarbon in water emulsion comprises forming said emulsion having a ratio by weight of hydrocarbon to water at least about 70:30.

5. The process of claim 3, wherein said step of forming said hydrocarbon in water emulsion comprises forming said emulsion having a ratio by weight of hydrocarbon to water between about 70:30 and about 30:70.

6. The process of claim 3, wherein said step of providing said bioactive material comprises providing a water phase for said emulsion which contains said bioactive material, and wherein said step of forming said emulsion exposes said liquid hydrocarbon to said bioactive material.

7. The process of claim 3, wherein said inorganic sulfur compounds are present in said water phase.

8. The process of claim 1, wherein said liquid hydrocarbon is selected from the group consisting of bitumen, heavy crude, medium crude, Diesel fuel, gasoline, coal slurry and mixtures thereof.

9. The process of claim 1, wherein said liquid hydrocarbon is bitumen.

10. The process of claim 1, wherein said organic sulfur compounds include dibenzothiophene, and wherein said inorganic sulfur compounds include sulphates, hydrogen sulfide and mixtures thereof.

11. The process of claim 1, further comprising the step of separating said inorganic sulfur compounds from said liquid hydrocarbon.

12. The process of claim 1, wherein said liquid hydrocarbon further comprises a C15+ fraction, and wherein said exposing step reduces said C15+ fraction.

13. The process of claim 1, wherein said effective conditions include a temperature between 30° C. and 50° C. and a pH between 7.0 and 8.0.

14. The process of claim 1, wherein the broth medium comprises a meat extract/bacto-peptone medium.

15. A bioactive material comprising a purified derivative of *Alcaligenes xylosoxidans* INTS-1 (PTA 4669), which is effective, at a temperature between 30° C. and 50° C. and a pH between 7.0 and 8.0, in breaking down carbon-sulfur-carbon bonds in organic sulfur-containing compounds, wherein the derivative is a product of incubation of a strain of said *Alcaligenes xylosoxidans* with exposure to a broth medium.

16. The bioactive material of claim 15, wherein the broth medium comprises a meat extract/bacto-peptone medium.

17. A bioactive material comprising a purified derivative of *Alcaligenes xylosoxidans* INTS-1 (PTA 4669) which is viable in oil and is active in breaking down carbon-sulfur-carbon bonds in organic sulfur containing compounds, wherein the derivative is a product of incubation of a strain of said *Alcaligenes xylosoxidans* with exposure to a broth medium.

18. The bioactive material of claim 17, wherein the broth medium comprises a meat extract/bacto-peptone medium.

* * * * *